United States Patent [19]

Cullinan et al.

[11] Patent Number: 5,596,106

[45] Date of Patent: Jan. 21, 1997

[54] CANNABINOID RECEPTOR ANTAGONISTS

[75] Inventors: George J. Cullinan, Trafalgar; Kennan J. Fahey; Gary A. Koppel, both of Indianapolis, all of Ind.

[73] Assignee: Eli Lilly and Company, Indianapolis, Ind.

[21] Appl. No.: 477,964

[22] Filed: Jun. 7, 1995

Related U.S. Application Data

[63] Continuation-in-part of Ser. No. 275,895, Jul. 15, 1994, abandoned.

[51] Int. Cl.$^6$ .................... C07D 333/56; C07D 307/80; C07D 333/62
[52] U.S. Cl. .................... 549/57; 549/51; 549/468
[58] Field of Search .................... 549/57, 51, 74, 549/468, 469; 514/443, 469

[56] References Cited

U.S. PATENT DOCUMENTS

| | | | |
|---|---|---|---|
| 3,331,854 | 7/1967 | Huffman et al. | 549/468 |
| 3,394,125 | 7/1968 | Crenshaw I | 549/468 |
| 3,413,305 | 11/1968 | Crenshaw II | 549/51 |
| 3,448,190 | 6/1969 | Baron et al. | 514/469 |
| 4,133,814 | 1/1979 | Jones et al. | 260/326.55 |
| 4,358,593 | 11/1982 | Jones et al. | 546/202 |
| 4,380,635 | 4/1983 | Peters | 546/202 |
| 4,418,068 | 11/1983 | Jones | 424/267 |
| 5,223,510 | 6/1993 | Gubin et al. | 514/299 |
| 5,308,866 | 5/1994 | Lesieur et al. | 514/469 |
| 5,470,854 | 11/1995 | von Angerer et al. | 549/51 |
| 5,472,962 | 12/1995 | Koizumi et al. | 549/51 |

FOREIGN PATENT DOCUMENTS

| | | |
|---|---|---|
| 2131795 | 6/1984 | United Kingdom . |
| WO95/10513 | 4/1995 | WIPO . |

OTHER PUBLICATIONS

Jones, C., et al., *J. Med. Chem.*, 27: 1057–1066 (1984), "Antiestrogens. 2. Structure Activity Studies in a Series of 3–Aroyl–2–arylbenzo [b]thiophene Derivatives Leading to [6–Hydroxy–2–(4–hydroxyphenyl)benzo[b]thien–3–yl][4–[2–(1–piperidinyl)ethosy]–phenyl]methanone Hydrochloride (Ly156758), a Remarkably Effective Estrogen Antagonist with Only Minimal Intrinisic Estrogenicity."

Monge, A., et al., *J. Heterocyclic Chem.*, 22: 1445–1451 (1985), "About the Synthesis of [1,2]Diazepinoindole Derivatives from Ethyl 2–(Methylindole)acetate, 2–Indole and 3–Indoleacetohydrazones."

Chambers, M., et al., *J. Chem. Soc. Perkin Trans.*, 1: 1365–1366 (1989), "Nickel Catalysed Conversion of Phenol Triflates into Aromatic Nitriles and Acids."

Durani, N., et al., *Indian J. of Chem.*, 22B: 489–490 (1983), "A Convenient Synthesis of 2–Aryl–3–aroylbenzo[b]furans."

Jones, C., et al., *J. Med. Chem.*, 35: 931–938 (1992), "Antiestrogens. 3. Estrogen Receptor Affinities and Antiproliferative Effects in MCF–7 Cells of Phenolic Analogues of Trioxifene, [3,4–Dihydro–2–(4–methoxylphenyl)–1–naphthalenyl][4–[2–(1–pyrrolidinyl)ethoxy]–phenyl]methanone."

Astoin, J., et al., *J. Heterocyclic Chem.*, 14: 861–869 (1977), "Recherches sur le benzofuranne. LIX. Orientation de l'aroylation de l'ethyl–2 benzofuranne selon la nature du chlorure d'aroyle utilise (1)."

Lynn, A., et al., *Journal of Pharmacology and Experimental Therapeutics*, 268(3): pp. 1612–1623 (1993), "Localization of Cannabinoid Receptors and Nonsaturable High–Density Cannabinoid Binding Sites in Peripheral Tissues of the Rat: Implications for Receptor–Mediated Immune Modulation by Cannabinoids".

Mechoulam, R., et al., *CNS Drugs*, 2(4): pp. 255–260 (1994), "Role and Therapeutic Implications for CNS Disorders".

Mechoulam, R., et al., *Biochemical Pharmacology*, 48(8): pp. 1537–1544 (1994), "Search for Endogenous Ligands of The Cannabinoid Receptor".

Compton, D., et al., *The Journal of Pharmacology and Experimental Therapeutics*, 263(3): pp. 1118–1126 (1992), "Aminoalkylindole Analogs: Cannabimimetic Activity of a Class of Compounds Structurally Distinct from $\rightarrow^9$–Tetrahydrocannabinol[1]".

Howlett, A., et al., *Tins at Neuroscience*, 13: pp. 420–423 (1990), "The cannabinoid receptor: biochemical, anatomical and behavioral characterization".

Felder, C., et al., *Proc. Natl. Acad. Sci.*, 90: pp. 7656–7660 (1993), "Anandamide, an endogenous cannabinoid receptor and stimulates receptor–mediated signal transduction".

*Primary Examiner*—José G. Dees
*Assistant Examiner*—Deborah Lambkin
*Attorney, Agent, or Firm*—Martin A. Hay; David E. Boone

[57] ABSTRACT

This invention discloses methods of using certain aryl-benzo [b]thiophene and benzo[b]furan compounds to block or inhibit cannabinoid receptors in mammals. It also discloses novel compounds which are antagonists of the cannabinoid receptors and also discloses pharmaceutical formulations which contain the compounds as an active ingredient.

5 Claims, No Drawings

CANNABINOID RECEPTOR ANTAGONISTS

This is a continuation-in-part of U.S. patent application Ser. No. 08/275,895 filed on Jul. 15, 1994, abandoned.

FIELD OF THE INVENTION

This invention relates to aryl-benzo[b]thiophene and benzo[b]furan compounds which are active antagonists of the CB-1 (cannabinol-1) receptor in the mammalian central nervous system.

BACKGROUND OF THE INVENTION

Cannabinoids are compounds derived from the *cannabis sativa* plant which is commonly known as marijuana. The most active chemical compound of the naturally ocurring cannabinoids is tetrahydrocannabinol (THC), particularly (−)-$\Delta^9$-THC. This compound was isolated and identified in the 1960's and since that time there has been an ever increasing scientific investigation of the effects and pharmacology of the cannabinols. However, prior to discovery of THC, the effects and pharmacology of marijuana use have been known for several thousand years. Both the uses and abuses of marijuana are recorded from the earliest human records. Marijuana based medicants have been known for centuries and have been a mainstay of many folk, herbal remedies.

Among the many beneficial pharmacological properties attributed to marijuana are: analgesia, lowering blood and intra-ocular pressure, and anti-emetic activity in both mammals and man. Indeed, currently, there is much debate over whether marijuana use should be legalized in certain cases, such as its use in cancer patients for ameliorating the nausea induced by chemotherapy or to lower intra-ocular pressure in glaucoma patients. After the elucidation of THC, several synthetic compounds were discovered and have been used clinically for the treatment of cancer patients, among these are: Nabilone, Nabortate and Levonantrodol. However, although these drugs are useful, they have to a greater or lesser extent some of the negative pharmacologic properties of THC and thus, are limited in their general use.

As marijuana's beneficial effects have been long known, so to its negative effects have been well documented. Notable in the negative pharmacology associated with marijuana (and later shown to be associated with THC) are: psychological distortions of perception, loss of short-term memory, loss of motor coordination, sedation, and euphoria. Long term use of marijuana is considered by many to lead to addiction. Throughout the long history of marijuana its use and abuse have been intertwined.

Until the 1980's, the mechanism by which the cannabinols, most specifically THC, acted on the central nervous system was obscure. With the advent of very potent, radio-labelled, synthetic THC agonists (CP 55,940, HU210, and HU211), the search for the molecular basis of THC pharmacology began to be elucidated.

In 1988, it was determined that there was a specific receptor which bound $\Delta^9$ THC as well as the other synthetic agonists. Using radio autography, the cannabinol receptor was found to be localized in the hippocampus area of the rat brain (see: Herkenham, M., Ann. NY Acad. Sci., 645: p. 19–32 (1992) and references therein). (For a review of this chronology, see: Mechoulam, R., et al., CNS Drugs, 2(4), p. 255–260 (1994)). Subsequently, it was discovered that there was another, distinct receptor which appears to be primarily located in the peripheral tissues, especially in the immune system (see: Lynn, A. B. and Herkenham, M., J. Pharm. and Exp. Ther., 268(3), p. 1612–1623 (1994)). Both receptors have been purified, amino acid sequenced, cloned, and expressed in experimental cell lines. The two receptors which bind both the cannabinoids and their synthetic agonists have been designated as: CB-1, the receptor located in the central nervous system, and CB-2, the receptor found in peripheral tissues. It is generally agreed that much of the cannabinoid pharmacology, associated with its central nervous system effects and which is most germane to this invention, is directly related to the action of the CB-1 receptor. Synthetic and natural compounds which are agonists of the CB-1 receptor, demonstrate the expected experimental and human pharmacology, while closely related compounds which bind poorly to CB-1 do not. (For a review of these findings, see: Mechoulam, R., et al., Biochem. Pharm., 48(8), p. 1537–1544 (1994)).

In 1992, it was discovered that the endogenous ligand for the CB-1 receptor is anandamide, N-ethanolamine amide of arachidonic acid (see: Devane, W. A., et al., Science, 258, p. 1946–1949. (1992)). The discovery of this new neurotransmitter has initiated an intense investigation into the regulation and pharmacology of anandamide. Preliminary results indicate that animals treated with exogenous anandamide demonstrate behavior similar to those treated with cannabinoids. Because of the parallelism of cannabinoid and anandamide pharmacology and the area of the location in the brain of the CB-1 receptor, there is a growing body of evidence that anandamide is a key regulator of functions such as sensory perception, cognition, memory, pain perception, and mood modulation. Since it is very clear in humans what the agonism of the CB-1 receptor does with cannabinoids, it would seem reasonable by the same extrapolation to predict the likely pharmacology of antagonists of the CB-1 receptor would possess.

Therefore, in patients suffering from loss of sensory perception, cognition, and mood changes such as lethargy and depression, conditions which are often associated with the use of marijuana, there is a strong implication that a controlling factor exacerbating these events would be an inappropriately high or unregulated control of anandamide - CB-1 interaction. An anandamide - CB-1 antagonist would be useful in conditions where patients exhibit these symptoms.

There are two reports in the art of cannabinol receptor partial agonists or antagonists which are not either anandamide or cannabinoid analogs. The first of these compounds, an aminoalkylindole, a partial agonist, (see FIG. 1) is revealed in Pacheco, M., et al., J. Pharmacol. Exp. Ther., 257, p. 170–183 (1991) and Compton, D. R., et al., J. Pharmacol. Exp. Ther., 263, p. 1118–1126 (1992). The antagonist, a halo-aryl pyrazole (SR 141716A) (see FIG. 2), was revealed in a patent application EP 0576357A1. The CB-1 antagonist, SR141716A, has been shown to block the actions of both cannabinoids and anandamide in in vivo and in vitro models (see: Rinaldi-Carmons, M., et al., FEBS Letters, 350, p. 240–244 (1994)).

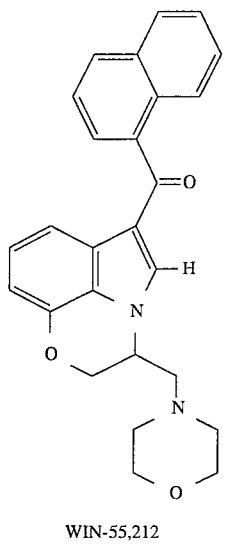

WIN-55,212

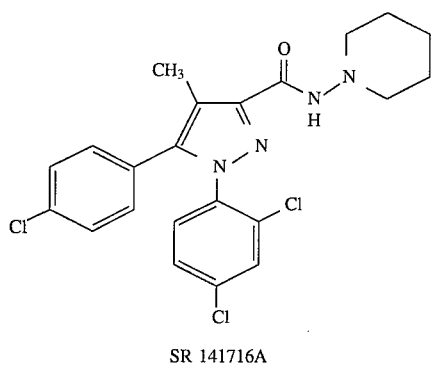

SR 141716A

SUMMARY OF THE INVENTION

This invention provides a method of antagonizing one or more of the actions of anandamide at cannabiniol-1 receptors in a mammal, which comprises administering an effective amount of a compound of formula

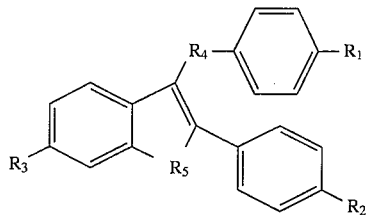

in which
$R^1$ is $C_1-C_4$ alkoxy, trifluoromethylsulfonyloxy, hydroxy or cyano;
$R^2$ and $R^3$ are each independently $C_1-C_4$ alkyl or $C_1-C_4$ alkoxy;
$R^4$ is CO, CHOH or $CH_2$; and
$R^5$ is O or S, provided that when $R^1$ is hydroxy, $R^5$ is O.

Certain compounds of formula I are believed to be novel and are provided as another aspect of the invention. Accordingly, the present invention provides a compound of formula I wherein
$R^1$ is cyano;
$R^2$ and $R^3$ are each individually $C_1-C_4$ alkyl or $C_1-C_4$ alkoxy;
$R^4$ is carbonyl; and $R^5$ is oxygen or sulfur.

The invention also provides pharmaceutical formulations which include a novel compound of formula (I) as active ingredient in combination with a pharmaceutically acceptable carrier, diluent or excipient.

DETAILED DESCRIPTION OF THE INVENTION

The term "$C_1-C_4$ alkyl" represents a straight or branched alkyl chain having from one to four carbon atoms. Typical straight or branched $C_1-C_4$ alkyl groups include methyl, ethyl, n-propyl, isopropyl, n-butyl, isobutyl, sec-butyl and t-butyl.

The term "$C_1-C_4$ alkoxy" represents an oxygen atom connected directly to the $C_1-C_4$ alkyl group to form an ether moiety. Examples of $C_1-C_4$ alkoxy groups include methoxy, ethoxy, propoxy and butoxy.

$R^1$ is preferably methoxy, trifluoromethylsulfonyloxy, hydroxy or cyano. Most preferably $R^1$ is cyano.

$R^2$ is preferably methyl or methoxy.

$R^3$ is preferably methoxy.

$R^4$ is preferably carbonyl.

$R^5$ is preferably —O—.

Particularly preferred compounds are those in which $R^1$ is cyano, $R^2$ is methoxy, $R^3$ is methoxy, $R^4$ is carbonyl and $R^5$ is O; or $R^2$ is methyl, $R^3$ is methoxy, $R^4$ is carbonyl and $R^5$ is O; or $R^2$ is methoxy, $R^3$ is methoxy, $R^4$ is carbonyl and $R^5$ is S.

The compounds of formula I belong to two related chemical groups, the benzothiophene group and the benzofuran group.

1. Benzothiophene Group

This group of compounds includes all of the compounds where $R^5$ is S, shown below:

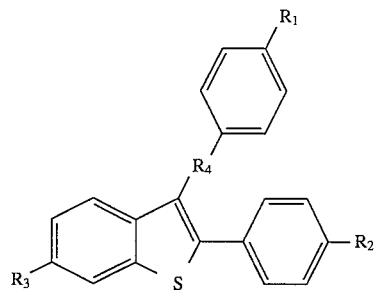

wherein $R^1-R^4$ are as defined above. Of this group of preferred compounds, the most preferred compound has the $R^1$ group is CN; methoxy groups at $R^2$ and $R^3$; and $R^4$ is carbonyl. This substitution defines the most preferred compound, [6-methoxy-2-(4-methoxyphenyl)benzo(b)thien-3-yl][4-cyanophenyl]methanone which has the following structure:

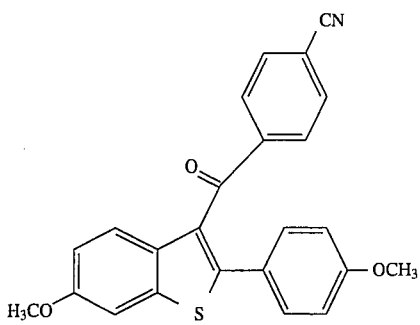

The general scheme for synthesizing the preferred benzothiophene compounds is shown as Scheme I:

As shown in the above Scheme I the starting material of 4-methoxyacetophenone was brominated in methanol to form the halo intermediate shown. An aryl sulfide and base is reacted with this intermediate to form the diaryl intermediate linked by the sulfur - acetyl bridge. Cyclization of this intermediate to the desired benzo(b) thiophene backbone is achieved by reacting with polyphosphoric acid at elevated temperatures. As shown, the 4-methoxyphenyl moiety tends to arrange via cationic rearrangement to the 2-position of the benzothiophene.

The 2-aryl-benzo(b) thiophene intermediate is then reacted with an aryl acyl halide under Friedel-Crafts conditions. The electrophilic substitution takes place primarily on the three position ($C_3$) of the thiophene ring as shown. To produce the most preferred compound of this group, the 4-methoxy group is substituted by a cyano or nitrile group, Scheme I

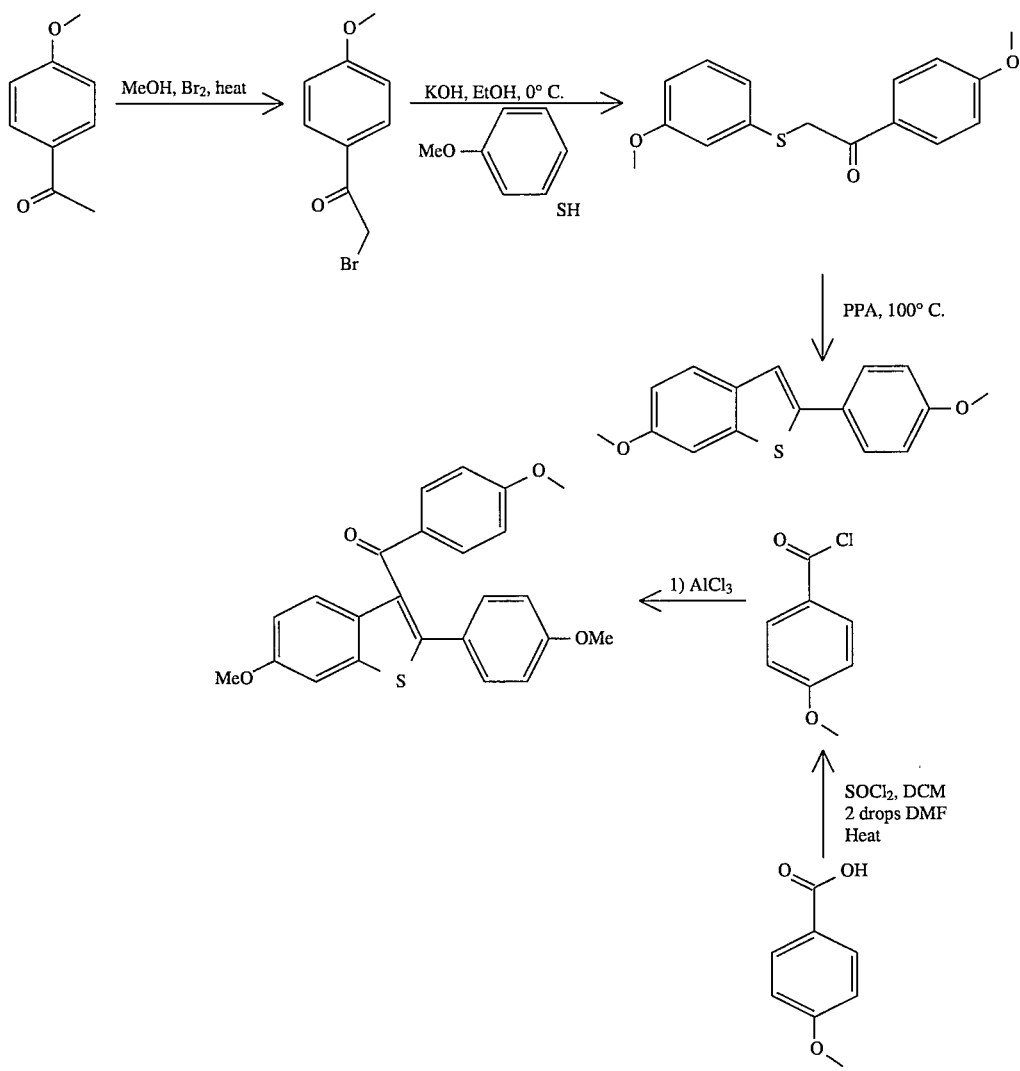

Benzothiophene synthesis, such as in the scheme shown above, is also well documented in the art. Jones, et al., J. Med. Chem., 1984, Vol. 27, No. 8, pp. 1057–1066, disclose the basic scheme shown above, while variations of this scheme are found in U.S. Pat. Nos. 4,133,814; 4,358,593; 4,380,635; and 4,418,068.

which requires the presence of more catalyst due to low electrophility.

2. Benzo(b)furan Group

The general schemes for synthesizing compounds of this group is shown below as Scheme II:

SCHEME II

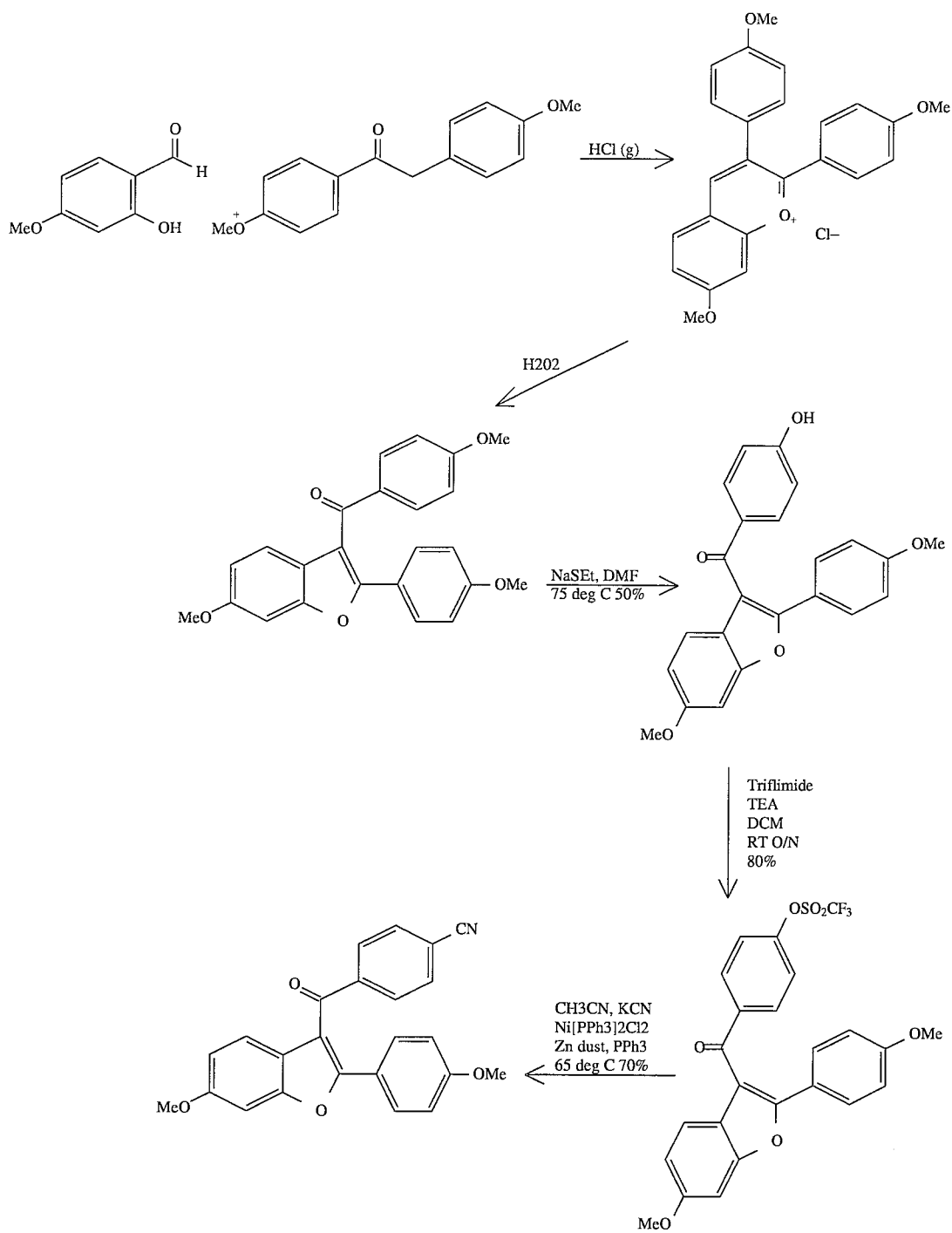

The above scheme generally depicts the synthesis of the most preferred compound of the benzofuran group, [6-methoxy-2-(4-methoxyphenyl)benzo[b]furan-3-yl]-3(4-cyanophenyl)methanone. Synthesis of the 3-(4-methoxyphenyl) intermediate compound is described in detail by Durani and Kapil, A convenient Synthesis of 2-Aryl-3 Aroylbenzo[b]furans, Indian Journal of Chemistry, Vol. 22B, May 1983, pp. 489–490. As shown in Scheme II, 2-hydroxy-4-methoxy benzaldehyde is reacted with a diaryl ketone in a strong acid to form the benzopyrilium salt intermediate compound shown. This intermediate is then oxidized to produce the [6-methoxy-2-(4-methoxyphenyl)-benzo[b]furan-3-yl]-3-(4-methoxyphenyl)methanone intermediate which is well-known in the art.

This intermediate is then dealkylated by a well-known procedure to form the 4-hydroxy intermediate shown. A two-step process is then employed to convert the 4-hydroxy moiety to a nitrile group as shown above. First the hydroxy group is converted to a triflate ester derivative and then this compound is reacted with a cyanide source in the presence of a catalyst to complete the conversion to the preferred compound. The general procedure for converting a methoxy moiety to a cyano moiety is shown in part in Chambers and Widdowson, Nickel Catalysed Conversion of Phenol Triflates to Aromatic Nitriles and Acids, J. Chem, Soc. Perkin Trans. I, 1989, p. 1365. Preferred reagents for the conversion are triflimide ((CF$_3$SO$_2$)$_2$NPhenyl) and triethylamine in a non-polar solvent to effect the hydroxy-triflate conversion; acetonitrile, potassium cyanide, and Nickel-bis-triphenylphosphine chloride with zinc dust metal and triphenyl phosphine to effect the triflate to cyano conversion. As with scheme I, derivative compounds of the preferred compound are easily prepared by one skilled in the art or by the same chemistry.

Other benzo[b]furan derivatives are depicted in Scheme III shown below:

SCHEME III

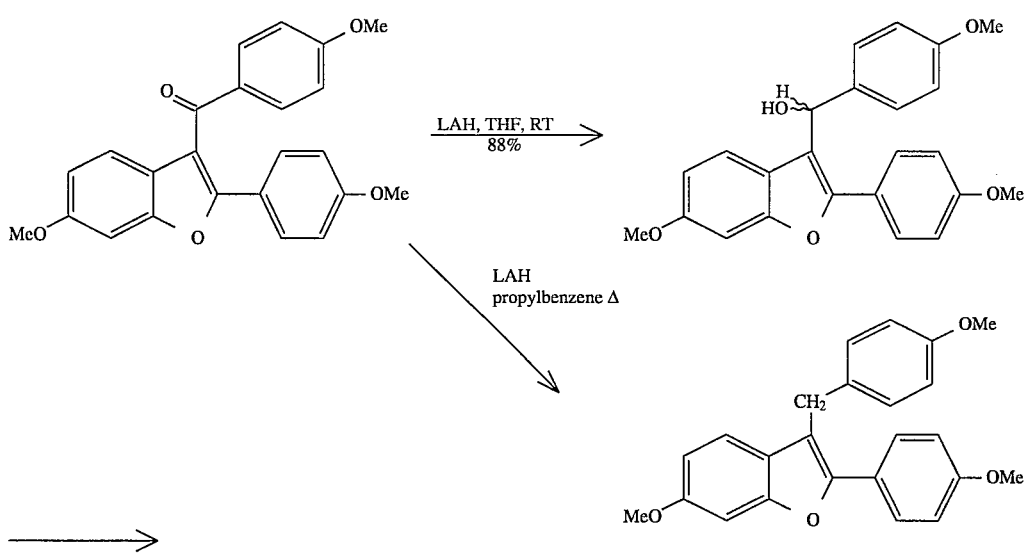

The above scheme depicts the synthesis of various benzo[b]furan derivatives with different bridges between the furan ring and the 3-(4-methoxyphenyl)ring. As shown in Schemes I and II, the typical bridge is a carbonyl group. Scheme III depicts the formation of 2 different bridge groups, namely, the carbinol and methylene. All of these compounds are preferably formed from the (4-methoxyphenyl)methanone base intermediate by the processes shown. Detailed descriptions of these processes, as with all other processes in Schemes I–II may be seen in the specific Examples later in this specification.

Finally, the preferred benzo[b]furan compounds can be synthesized via Friedel-Crafts acylation of the benzo[b]furan intermediate as outlined generally in Scheme IV below, and defined in detail in the specific Examples.

SCHEME IV

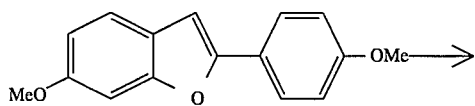

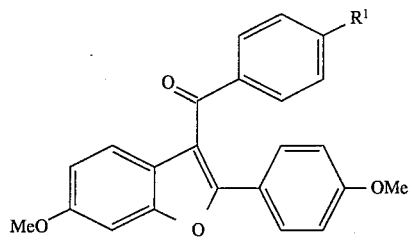

The general procedures for the above Scheme IV are referenced in J. Astoin, J. Heterocyclic Chemistry, 1977, Vol. 14, pp. 861–869.

The specific examples which follow are not to be considered as limiting the invention, but are merely illustrative of the best mode of synthesis of the most preferred compounds at this time.

EXAMPLE 1

Synthesis of α-(3'-Methoxyphenoxy)-4-methylacetophenone 51.05 g (0.24 mol) of 4-methyl-α-bromoacetophenone was dissolved in 200 mL of anhydrous (dimethyl formamide) DMF and 35 g (0.28 mol) of 3-methoxyphenol was added. The reaction mixture was stirred with a mechanical stirrer and 80 g (0.58 mol) of anhydrous K$_2$CO$_3$ was added. The reaction was allowed to proceed at ambient temperature and under an atmosphere of nitrogen. After eighteen hours, the reaction mixture was filtered to remove the inorganic salts. The DMF was removed by evaporation in vacuo, the resulting thick oil was dissolved in 250 mL of EtOAc and washed with brine. The EtOAc layer was removed and dried by filteration through anhydrous Na$_2$SO$_4$ and the solvent was removed by evaporation. The resulting oil was crystallized from Et$_2$O, which yielded 37 g of the title compound as a light yellow solid.

PMR: consistent with the proposed structure
MS: m/e=256 (M+) FD
EA: Calc: C, 74.98; H, 6.29 Found: C, 75.17; H, 6.38

EXAMPLE 2

Synthesis of 6-Methoxy-2-(4-methylphenyl)benzo[b]furan 30 g (0.12 mol) of 2-(3-Methoxyphenoxy)-4'-methylacetophenone was dissolved in 300 mL of xylene and 45 g of polyphosphoric acid (PPA) was added. The reaction mixture was stirred with a magnetic stirrer and kept under an atmosphere of nitrogen. The reaction was heated to reflux (135° C.) for eighteen hours. The reaction was allowed to cool to about 90° C. and 500 mL of water was added. The reaction was stirred until all the PPA dissolved in the water layer. The xylene layer was removed and extracted twice with water. The xylene layer was dried by filteration through anhydrous $Na_2SO_4$ and evaporated to remove the solvent. The resulting solid was crystallized from hot ethyl acetate (EtOAc), which yielded 5 g of the title compound as a white solid.

PMR: consistent with the proposed structure
MS: m/e=238 (M+) FD
EA: Calc: C, 80.65; H, 5.92 Found: C, 80.57; H, 5.97
$C_{16}H_{14}O_2$ MW=238.29

EXAMPLE 3

Synthesis of [6-Methoxy-2-(4-methylphenyl)benzo[b]furan-3-yl][4-cyanophenyl]methanone One gram (4.2 mmol) of 6-Methoxy-2-(4methylphenyl)benzo[b]furan was dissolved 25 mL of dichloromethane and 830 mg (5.0 mmol) of 4-cyanobenzoyl chloride was added. The reaction was stirred and kept under a nitrogen atmosphere. 2.75 mL (25 mmol) of $TiCl_4$ was slowly added to the reaction mixture. The reaction was allowed to proceed for four hours and quenched by the addition of 5 mL of methanol (MeOH). The solvents were removed by evaporation and the crude material was chromatographed on a silica gel column eluted with hexane-EtOAc (9:1). The desired fractions were determined by tlc and combined and evaporated to a solid. The resulting product was crystallized from diethyl ether ($Et_2O$). This yielded 325 mg of the title compound as yellow powder.

PMR: consistent with the proposed structure
MS: m/e=368 (M+) FD
EA: Calc: C, 78.46; H, 4.66; N, 3.81 Found: C, 78.28; H, 4.61; N, 3.52.

EXAMPLE 4

Synthesis of [6-Methoxy-2-(4-methoxyphenyl)-benzo[b]furan-3-yl]-3-(4-hydroxyphenyl)-methanone A suspension of 2 g of [6-Methoxy-2-(4-methoxyphenyl)benzo[b]furan-3-yl]-3-(4-methoxyphenyl)-methanone 5.15 mmol) and 1.3 g sodium ethanethiol (15.45 mmol) in 40 mL of DMF was heated to 80° C., checking by TLC 35% ethyl acetate:hexane every 20 minutes. When the starting material was consumed after 4 hours, the mixture was allowed to cool to room temperature, diluted with 150 mL. ethyl acetate, and washed twice with 1N $H_2SO_4$ (100 mL.). The organic layer was then dried on $Na_2SO_4$ and rotovaped to a brown oil, then purified by gravity chromatography with silica, 35% ethyl acetate:hexane. 1.15 g yield (60%) of the title compound as a bright yellow solid. PChem: NMR QE300 MHz in d6-DMSO: (3.85 ppm, s, 3H), (3.90 ppm, s, 3H), (6.85 ppm, d, 2H), (6.95 ppm, dd, 1H), (7.00 ppm, d, 2H), (7.30 ppm, ds, 1H), (7.40 ppm, s, 1H), (7.60 ppm, d, 2H), (7.75 ppm, d, 2H).

EXAMPLE 5

Synthesis of [6-Methoxy-2-(4-methoxyphenyl)-benzo[b]furan-3-yl]-3-(phenyl-4-triflate)-methanone A solution of 1.15 grams (3.07 mmol) of the Example 4 intermediate was dissolved in 40 mL. of methylene chloride with 0.92 mL. of tri-ethyl amine (6.61 mmol). To this was added a solution of 1.15 g of triflimide (3.23 mmol) in 10 mL. methylene chloride over 15 minutes. After addition, the mixture was allowed to stir at room temperature for 48 hours. The mixture was then diluted with 100 mL methylene chloride, washed twice with 1N $H_2SO_4$, twice with deionized water, twice with saturated $NaHCO_3$, then once more with water. Dry on $Na_2SO_4$ to yield 1.4 grams (89.7%) of the title compound yellow amorphous material. PChem: NMR QE300 MHz in $CDCl_3$: (3.80 ppm, s, 3H), (3.90 ppm, s, 3H), (6.75 ppm, d, 2H), (6.95 ppm, dd, 1H), (7.10 ppm, ds, 1H), (7.20 ppm, d, 2H), (7.45 ppm, d, 2H), (7.60 ppm, d, 1H), (7.85 ppm, d, 2H). MS FD+=506.

EXAMPLE 6

Synthesis of [6-Methoxy-2-(4-methoxyphenyl)-benzo[b]furan-3-yl]-3-(4-cyanophenyl)-methanone A solution of 1.1 g of (2.17 mmol) of the Example 5 compound in 4 mL. of dry acetonitrile with 156 mg KCN (2.39 mmol), 71 mg of nickel triphenylphosphine dichloride (0.109 mmol), 57 mg of triphenylphosphine (0.217 mmol), and 43 mg of zinc dust (0.652 mmol) was heated to 65° C. for 2 hours. The mixture was then allowed to cool to room temperature, diluted with 100 mL. of methylene chloride, washed twice with water, and dried on $Na_2SO_4$. The mixture was then purified on a silica plug with flash chromatography using 100% methylene chloride, rotovaped dry, and crystallized from 100% ethyl acetate to yield 580 mg of the title compound (70%). PChem: NMR QE300 MHz in d6-DMSO: (3.75 ppm, s, 3H), (3.85 ppm, s, 3H), (6.85 ppm, d, 2H), (6.95 ppm, dd, 1H), (7.35 ppm, ds, 1H), (7.45 ppm, d, 2H), (7.50 ppm, d, 1H), (7.80 ppm, s, 4H). MS FD+=384. EA calculated for $C_{24}H_{17}NO_4$ (Theory/Found): C, 75.19/75.35; H, 4.47/4.52; N, 3.65/3.66.

EXAMPLE 7

Synthesis of [6-methoxy-2-(4-methoxyphenyl)benzo[b]thien-3-yl][4-methoxyphenyl]methanone A solution of 1.54 g (9 mmol) of 6-methoxy-2-(4-methoxyphenyl)benzo[b]thiophene and 1.62 g (6 mmol) of p-anisoyl chloride in 100 mL of methylene chloride was prepared and cooled to 0° C. Over 5 minutes, 1.20 g (9 mmol) of $AlCl_3$ was added in small portions. After 1 hour, the reaction mixture was poured over 150 mL of ice water and extracted three times with 75 mL portions of methylene chloride. The methylene chloride extracts were combined and washed with 30 mL of 1N NaOH, then with water. The organic layer was dried with magnesium sulfate and evaporated to dryness. The crude product was chromatographed on silica eluted with 30% EtOAc in hexane. The product was crystallized from acetone-methanol. This yielded 2.11 g of the title compound as a light yellow solid.

PMR: consistent with the proposed structure
MS: m/e=404 (M+)
EA: Calc: C, 71.27; H, 4.98; S, 7.93; O, 15.82 Found C, 71.50; H, 5.00; S, 7.98; O, 15.77
$C_{24}H_{20}O_4S$

EXAMPLE 8

Synthesis of
[6-methoxy-2-(4-methoxyphenyl)benzo[b]thien-3-yl][4-hydroxyphenyl]methanone A solution of 0.4 g (1 mmol) of [6-Methoxy-2-(4-methoxyphenyl)benzo[b]thien-3-yl][4-methoxyphenyl]methanone in 2 mL of DMF was added to a solution of 3 mL of 0.5M sodium ethanethiol in DMF. The reaction mixture was heated to 80° C. for 4 hours. The reaction mixture was allowed to cool and diluted with 10 mL of water and 10 mL of EtOAc and neutralized with 1N HCl. The reaction mixture was extracted three times with 30 mL portions of EtOAc. The combined organic extracts were washed four times with 20 mL portions of brine and dried with MgSO$_4$ and evaporated to dryness. The crude product was chromatographed on silica eluting with 30% EtOAc in hexane, and evaporated to dryness. This yielded 0.31 g of the title compound as a yellow solid.

PMR: consistent with the proposed structure
MS: m/e=390 (M+) FD
EA: Calc: C, 70.75; H, 4.65 Found: C, 70.93; H, 4.56
$C_{23}H_{18}O_4S$

EXAMPLE 9

Synthesis of
[6-Methoxy-2-(4-methoxyphenyl)benzo[b]thien-3-yl][4-trifluoromethylsulfonyloxyphenyl]methanone A solution was prepared of 3 g (7.7 mmol) of [6-methoxy-2-(4-methoxyphenyl)benzo[b]thien-3-yl][4-hydroxyphenyl]methanone in 100 mL of methylene chloride and 1.57 g (15.5 mmol) of triethylamine. A solution of 2.8 g (7.72 mmol) of triflimide in 50 mL of methylene chloride was slowly added to the reaction mixture over a period of 30 minutes. The reaction, under an atmosphere of nitrogen and at room temperature, was allowed to proceed for 16 hours. The reaction mixture was washed with 100 mL of 1N H$_2$SO$_4$, then three times with 100 mL portions of 2N NaOH and finally with 100 mL of water. The organic layer was dried with anhydrous Na$_2$SO$_4$ and the product allowed to crystallize out. This yielded 2.5 g of the title compound as a yellow solid.

PMR: consistent with the proposed structure
MS: m/e=522 (M+) FD
EA: Calc: C, 55.17; H, 3.28 Found: C, 54.37; H, 3.21

EXAMPLE 10

Synthesis of
[6-Methoxy-2-(4-methoxyphenyl)benzo[b]thien-3-yl][4-cyanophenyl]methanone A suspension of 2 g (3.83 mmol) of the compound of example 7 was prepared in 5 mL of anhydrous acetonitrile with 274 mg (4.21 mmol) of KCN, 125 mg (0.19 mmol) of nickel triphenylphosphine dichloride, 101 mg (0.38 mmol) of triphenylphosphine, and 38 mg (0.58 mmol) of zinc dust. The reaction mixture was heated to 65° C. for 90 minutes under a nitrogen atmoshere. The reaction mixture was allowed to cool to room temperature and was diluted with 100 mL of methylene chloride. The reaction mixture was filtered and washed twice with 150 mL portions of water. The organic layer was dried with anhydrous Na$_2$SO$_4$. The crude product was recrystallized twice from MeOH. This yielded 1.1 g of the title compound as a yellow powder.

PMR: consistent with the proposed structure
MS: m/e=399 (M+) FD
EA: Calc: C, 72.16; H, 4.29; N, 3.51 Found: C, 71.96; H, 4.33; N, 3.50
$C_{24}H_{17}NO_3S$

EXAMPLE 11

Alternate Synthesis of
[6-Methoxy-2-(4-methoxyphenyl)benzo[b]furan-3-yl][4-cyanophenyl]methanone A solution of 160 g (0.63 mol) of 6-methoxy-2-(4-methoxyphenyl)benzo[b]furan and 154.3 g (0.93 mol) of 4-cyanobenzoyl chloride in 3 L of methylene chloride was prepared. To this solution, 203.6 mL (1.85 mol) of TiCl$_4$ was slowly added. The reaction mixture was heated to reflux under a nitrogen atmoshere for a period of four hours. The reaction mixture was poured unto 3 kg of ice and allowed to quench for sixteen hours. The organic layer was separated and washed twice with 5 L portions of 20% NaHCO$_3$ solution and finally washed with 5 L of brine. The organic layer was dried with anhydrous MgSO$_4$ and evaporated to an oil. The crude product was chromatographed on a silica gel column eluted with 20% EtOAc-CH$_2$Cl$_2$. This yielded 156 g, which was further purified by rechromatography on a silica gel column eluted with 20% EtOAc-Et$_2$O and crystallized from the eluting solvent. This yielded 100.1 g of the title compound as a yellow powder.

EXAMPLE 12

Synthesis of
6-Methoxy-2-(4-methoxyphenyl)benzo[b]thien-3-yl][4-n-propyloxyphenyl]methanone A solution of 1.17 g (3 mmol) of [6-methoxy-2-(4methoxyphenyl)benzo[b]thien-3-yl][4-hydroxyphenyl]methanone in 20 mL of DMF was prepared. To the solution was added 1.03 g (7.50 mmol) of potassium carbonate and the mixture was heated to 100° C. After 15 minutes, 2.73 mL (30 mmol) of 1-bromopropane was added and reaction was heated for an additional 40 minutes. The reaction mixture was allowed to cool and filtered. The filterate was added to 25 mL of water and was extracted three time with 20 mL portions of EtOAc. The combined extracted were washed with brine, dried with MgSO4 and evaporated to a solid. This yielded an eighty percent yield of the title compound.

PMR: consistent with the proposed structure
MS: m/e=432 (M+) FD
EA: Calc: C, 72.20; H, 5.59 Found: C, 72.00; H, 5.65
$C_{26}H_{24}O_4S$

EXAMPLE 13

Synthesis of
[6-Methoxy-2-(4-methoxyphenyl)benzo[b]thien-3-yl][4-n-butyloxyphenyl]methanone In a manner identical with example 12, the title compound was prepared in 77% yield as a yellow solid.

PMR: consistent with the proposed structure
MS: m/e=446 (M+) FD
IR: 3011, 2963, 2938, 1599, 1476, 1254, 1166 cm$^{-1}$ (CHCl$_3$)

EXAMPLE 14

Synthesis of
[6-Methoxy-2-(4-methoxyphenyl)benzo[b]furan-3-yl][4-methoxyphenyl]methanone The title compound was prepared in a manner similar to that used in example 3, by using p-anisoyl chloride as the acylating agent.

EXAMPLE 15

Synthesis of
[6-Methoxy-2-(4-methoxyphenyl)benzo[b]furan-3-yl][4-methoxyphenyl]methanol A solution of 1 g (2.56 mmol) of [6-Methoxy-2-(4methoxyphenyl)benzo[b]furan-3-yl][4-methoxyphenyl]methanone was prepared in 25 mL of THF. To this solution, 1 g (25.4 mmol) of LiAlH$_4$ was added in small portions over a 10 minute period. The reaction was allowed to proceed at room temperature in a nitrogen atmosphere. After sixteen hours, the reaction was quenched by the addition of 5 mL of water. To this suspension was added 3 mL of 15% (w/w) NaOH and an additional 3 mL of water. This suspension was filtered. The resulting filtrate separated into two layers. The top (organic) layer was removed and evaporated to dryness. The crude product was chromatographed on silica gel eluted with CHCl$_3$. This yielded 880 mg of the title compound as a colorless gum.

PMR: consistent with the proposed structure
MS: m/e=390 (M+) FD
EA: Calc: C, 73.83; H, 5.68 Found: C, 74.10; H, 5.66

EXAMPLE 16

Synthesis of
[6-Methoxy-2-(4-methoxyphenyl)benzo[b]furan-3-yl][4-methoxyphenyl]methane A solution of 400 mg (1.02 mmol) of [6-Methoxy-2-(4-methoxyphenyl)benzo[b]furan-3-yl][4-methoxyphenyl] methanol was dissolved in 10 mL of n-propylbenzene and 200 mg (5.25 mmol) of LiAlH4 was added. The reaction mixture was heated to reflux under a nitrogen atmoshere for 45 minutes. After sixteen hours, the reaction was quenched by the addition of 5 mL of water. To this suspension was added 3 mL of 15% (W/N) NaOH and an additional 3 mL of water. This suspension was filtered. The resulting filterate separated into two layers. The top (organic) layer was removed and evaporated to dryness. The crude product was chromatographed on silica eluted with 20% EtOAc in hexane. The final product was crystallized from ether. This yielded 100 mg of the title compound as a solid with a low melting point.

PMR: consistent with the proposed structure
MS: m/e=374 (M+) FD

Procedures for synthesizing other Formula I compounds are either well-known in the art or are easily converted by following one of the above procedures with different reagents, dependent upon the desired end compound.

The compounds of the present invention are preferably formulated prior to administration. Therefore, another aspect of the present invention is a pharmaceutical formulation comprising a compound of formula I and a pharmaceutically-acceptable carrier, diluent, or excipient. The present pharmaceutical formulations are prepared by known procedures using well-known and readily available ingredients. In making the compositions of the present invention, the active ingredient will usually be mixed with a carrier, or diluted by a carrier, or enclosed within a carrier which may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing for example up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium sterate and mineral oil. The formulations can additionally include lubricating agents, wetting agents, emulsifying and suspending agents, preserving agents, sweetening agents, or flavoring agents. Compositions of the inventions may be formulated so as to provide quick, sustained, or delayed release of the active ingredient after administration to the patient by employing procedures well known in the art.

The compositions are preferably formulated in a unit dosage form, each dosage containing from about 5 to about 500 mg, more preferably about 25 to about 300 mg of the active ingredient. The most preferred unit dosage form contains about 10 to about 200 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier. The following formulation examples are illustrative only and are not intended to limit the scope of the invention in any way.

FORMULATION 1

Hard gelatin capsules are prepared using the following ingredients:

| | Quantity (mg/capsule) |
|---|---|
| active ingredient | 250 |
| Starch, dried | 200 |
| Magnesium stearate | 10 |
| Total | 460 mg |

The above ingredients are mixed and filled into hard gelatin capsules in 460 mg quantities.

FORMULATION 2

A tablet is prepared using the ingredients below:

| | Quantity (mg/tablet) |
|---|---|
| active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

FORMULATION 3

An aerosol solution is prepared containing the following components:

| | Weight % |
|---|---|
| active ingredient | 0.25 |
| Ethanol | 29.75 |
| Propellant 22 | 70.00 |
| (chlorodifluoromethane) | |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

FORMULATION 4

Tablets each containing 60 mg of active ingredient are made as follows:

| | |
|---|---|
| active ingredient | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules each containing 80 mg medicament are made as follows:

| | |
|---|---|
| active ingredient | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 sieve, and filled into hard gelatin capsules in 200 mg quantities.

FORMULATION 6

Suppositories each containing 225 mg of active ingredient may be made as follows:

| | |
|---|---|
| active ingredient | 225 mg |
| Staurated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions each containing 50 mg of medicament per 5 ml dose are made as follows:

| | |
|---|---|
| active ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

FORMULATION 8

An intravenous formulation may be prepared as follows:

| | |
|---|---|
| active ingredient | 100 mg |
| Mannitol | 100 mg |
| Purified water to total | 200 ml |

A variety of physiological functions have been shown to be influenced by stimulation of the cannabinoid receptors. The formula I compounds of the present invention are believed to possess the ability to treat a variety of disorders in mammals, including humans which are associated with cannabinoid stimulation. Such disorders include, without limitation, depression, cognitive dysfunction, loss of memory and poor alertness and sensory perception. The formula I compounds act as antagonists of the cannabinoid receptors.

Experiments were performed to demonstrate the antagonist activity of the formula I compounds at the cannabinoid receptors. The formula I compounds were tested for their ability to inhibit binding of [1α,2β-(R)-5α]-(−)-5-(1,1-dimethylheptyl)-2-[5-hydroxy-2-(3-hydroxypropyl)cyclohexylphenol(CP-55,940); and for their ability to increase cAMP accumulation in cells.

Cell Culture and Stable Expression of Cannabinoid Receptor Clones

Chinese hamster ovary cells (CHO) and murine Ltk cells were obtained from The American Type Culture Collection (Rockville, Md.). CHO cells were maintained in an atmosphere of 5% $CO_2$ in growth media consisting of Alpha-MEM substituted with 10% fetal calf serum, L-glutamine (2 mM) and penicillin (50 U/ml) and streptomycin (50 ug/ml). Ltk cells were cultured at 37° C., in 5% $CO_2$ in Dulbecco's modified essential medium (0.45% glucose) containing fetal bovine serum (10%), L-glutamine (2 mM), penicillin (50 U/ml) and streptomycin (50 ug/ml). The rat cannabinoid receptor cDNA was stably expressed in CHO cells. A 2.2 kilobase (kb) SstI-EcoR1 fragment containing the complete coding region of the human cannabinoid receptor gene was subcloned into the SstI and EcoR1 sites of the pCD-PS vector to created plasmid hSKR6pl which was transfected into CHO cells using calcium phosphate precipitation. Receptor-containing plasmids were co-transfected with plasmids containing the neomycin resistance gene created in a similar fashion. After transfection, the cells were selected with neomycin and the individual neomycin resistant colonies grown to establish cell lines. The human cannabinoid (CB-1) cDNA was stably expressed in L cells with the following construct designed to amplify receptor expression levels thereby reducing the number of cells required for radioligand binding analysis. A 2.2 kilobase (kb) SstI-EcoR1 fragment containing the complete coding region of the human cannabinoid receptor gene was subclones into the SstI and EcoR1 sites of the pCD-PS vector to create plasmid hSKR6pl. From hSKR6pl, a 3.3 kb SalI-NdeI fragment was removed, the ends blunted, and inserted into the blunted SalI site of the plasmid ptkmuARS-4. The resulting plasmid contained the receptor gene coding sequence flanked by the SV40 early region promoter and polyadenylation sequence originally engineered into the cloning vector pCD. This plasmid was transfected into murine Ltk cells by calcium phosphate precipitation. After transfection, L cells were selected in HAT medium. Individual HAT-resistant colonies were isolated after 3-4 weeks, grown to established cell lines, and cultured for at least 3 months to allow for expression of the receptor to stabilize.

Thus, two cell lines were established which expressed the human CB-1 receptor, i.e., the CHO and the Ltk.

Plasma Membrane Preparation

Ltk Cells, grown to confluency in 175 $cm^2$ culture flasks, were washed once with cold phosphate buffered saline and scraped in assay buffer (50 mM Tris, 5 mM EDTA, 5 mg/mL BSA, pH 7.4) with added 200 mM sucrose. Cells were then centrifuged at 1000×g for 10 minutes at 4° C. The supernatant was discarded and the pellet resuspended in ice cold assay buffer, homogenized with a Tekmar Tissumizer (Cincinnati, Ohio, USA) at 95% maximal speed for 30 seconds followed by centrifugation for 15 minutes, 2°–4° at 2000×g. The supernatant was centrifuged again for 30 minutes at 43,000×g. The pellet was resuspended in minimal volume of assay buffer containing 200 mM sucrose and stored at −80° until use.

All experiments were performed in glass test tubes, which were treated by soaking in dichloromethane/toluene (1:10 vol/vol) for 1 hour and then in methanol for 30 minutes, followed by a final rinse with 100% methanol. Test tubes were then allowed to air dry overnight before use.

Radioligand Binding Assays

Competition and saturation binding assays were performed with [$^3$H]CP55,940 as the labeled ligand. A rapid filtration binding assay was developed (see: Felder, C. C., et al., Proc. Natl. Acad. Su., 90, p. 7656–7660(1993) based on a previously published method with the following modifications. All ligands were diluted in assay buffer containing 50 mg/mL fatty acid-free BSA, with the final BSA concentration not exceeding 5 mg/mL. Assay solutions were incubated in silicone-treated test tubes for 1 hr at 30°, with a final assay volume of 0.5 mL and a final membrane concentration of 40–400 µg of protein/mL. Membranes were rapidly filtered over GF/B filters (Whatman, Maidstone, England) that had been pretreated for 3 hr with 0.1% polyethyleneimine (v/w) (pH 7.4), using an Inotech (Lansing, Mich.) 96 or 48-position cell harvester. Membranes were washed with 3×3 mL of ice-cold wash buffer j(50 mM Tris, 0.5 mg/ml BSA, pH 7.4). Filters containing washed membranes were transferred to scintillation vials, 1 mL of 0.1% (v/v) Triton X-100 was added to each vial, and vials were incubated overnight before addition of scintillation cocktail (Hydrofluor; National Diagnostics, Manville, N.J.). Protein concentrations were determined using the bioinchoninic acid protein reagent (Pierce, Rockford, Ill.), as described. Binding data were analyzed with the program LIGAND or with program GraphPad (GraphPad Software, San Diego, Calif.), which performs weighted nonlinear least squares curve-fitting to the general model of Feldman.

The results of the potent, specific binding of the compounds of formula I are demonstrated in Table 1.

TABLE 1

| Compound | $K_i$ versus [$H^3$] CP55,940 |
| --- | --- |
| Example 15 | 25800 nM |
| Example 16 | 5300 nM |
| Example 4 | 4120 nM |
| Example 7 | 3600 nM |
| Example 12 | 1540 nM |
| Example 8 | 950 nM |
| Example 5 | 490 nM |
| Example 13 | 430 nM |
| Example 3 | 134 nM |
| Example 6 | 170 nM |

Assay of cAMP Accumulation

The purpose of this assay is to be demonstrate the effect of CB-1 binding compound on the CB-1 signal tranduction pathway, i.e., to establish if the binding compound is working as an agonist or antagonist in vitro.

CHO cells were preincubated in growth media with forskolin ($10^{-6}$M) with or without anandamide for 4 hours Cyclic AMP accumulation was measured over 5 minutes after exchanging the growth media with serum free media containing forskolin ($10^{-6}$M) and anandamide, with or without antagonists as indicated. Data are the mean ±S.E. of three experiments performed in triplicate. The results for the compound of Example 6 are shown in Table 2. In this assay forskolin (FSK) raises the level of cAMP above the basal level (BSL). The addition of anandamide (ANM) inhibits the increase of cAMP induced by the forskolin. The compound of Example 6 inhibits the biological; action of anandamide, i.e., negates the decrease in cAMP caused by anandamide, with an $IC_{50}$ of approximately 500 nM.

TABLE 2

| Sample | cAMP Accumulation pM/mL |
| --- | --- |
| Baseline | <5 |
| Forskolin (FSK) | 30 |
| Anandamine (ANM) (1 µM) | <5 |
| FSK + ANM | 5 |
| FSK + Cmpd. 6 (100 µM) | 35 |
| Cmpd. 6 (100 µM) | 5 |
| FSK + ANM + Cmpd 6 | |
| Cmpd. 6 (10 nM) | 5 |
| Cmpd. 6 (100 nM) | 10 |
| Cmpd. 6 (1 µM) | 45 |
| Cmpd. 6 (10 µM) | 65 |
| Cmpd. 6 (100 µM) | 75 |

Effect on N-type Calcium Channel Currents

In this series of experiments, it is demonstrated that compounds of formula I, not only bind the CB-1 receptor and inhibit the signal transduction pathway of CB-1, when activated by its endogenous ligand, anandamide, but in addition, effect other nerve cell organelles under control of the CB-1 signaling pathway in vitro. Specifically, the compounds of formula I open the N-type calcium channels, which are closed by either anandamide or the cannabinoids (see: Mackie, K. and Hille, B., Proc. Natl. Acad. Sci., 89, p.3825–3829 (1992)).

Materials

DMEM was obtained from Biowhittaker and GIBCO, FBS from HyClone, bovine serum albumin (fatty-acid free), dimethylsulfoxide, and NEM from Sigma, PTX from List, ω-CgTX from Peninsula Labs, and tetrodotoxin from Calbiochem. WIN 55,212-2 was a gift from Sterling Research Group. CP 55,940 was a gift from Pfizer Central Research. Anandamide was synthesized as described previously. Purity was monitored using thin layer chromatography with an elution system of petroleum ether/ether/methanol (in a ratio of 6:40:4). Anandamide migrated as a single spot with $R_F$ of 0.5, as expected.

Cell Culture and Preparation

N18 (neuroblastoma cell line) cells (passages 32–41) were grown on glass coverslip fragments in DMEM plus 5% (fetal bovine serum) (FBS, using standard cell culture techniques. Six to 14 days before recording, cells were "differentiated" by changing the medium to DMEM plus 0.5% FBS plus 2% dimethylsulfoxide. In PTX (Pertussis Toxin) experiments, differentiated cells were grown for an additional 16–20 hours in medium containing 500 ng/ml PTX. Control cells were treated identically, except that neurons were provided by M. S. Shapiro (University of Washington, Seattle, Wash.).

Current Recording

Currents were recorded using the whole-cell voltage-clamp technique. Pipettes were pulled from hematocrit glass (VWR) and fire polished. The pipette solution contained (in mM) 100 CsCl, 10 EGTA, 5 $MgCl_2$, 40 HEPES, 3 $Na_2ATP$, and 0.2 GTP, pH 7.30 with CsOH. For recording, a coverslip containing cells was transferred to the recording chamber (200 µl) and constantly perfused at a rate of 1–2 ml/min with an external solution containing (in mM) 160 NaCl, 5 $CaCl_2$, 4 KCl, 1 $MgCl_2$, 10 HEPES, and 8 glucose, pH 7.35 with NaOH. Tetrodotoxin (200 nM) was added to block voltage-gated sodium currents, and bovine serum albumin (3 µM) was present in all recording solutions to decrease adsorption of cannabinoids. Subsequently the cannabinoid agonist WIN 55,212 and the compounds of this invention were added. $I_{Ca}$ was measured near the end of a 25-msec depolarizing pulse to 0 mV and was defined as that component of the current sensitive to 100 µM $CdCl_2$. Solution reservoirs were selected by means of a series of solenoid valves, and solution changes were accomplished in <1 min. In all experiments the cells were held under voltage clamp at a holding potential of −65 mV. Voltage protocols were generated and data were digitized, recorded, and analyzed using BASIC-FASTLAB (Indec Systems, Capitola, Calif.). Currents were sampled at 4 kHz and junction potentials are uncorrected. To control for potential response variations with passage number and duration of differentiation, experimental and control measurements were alternated whenever possible. Where appropriate, data are expressed as mean±standard error. [It has been shown in this type of experiment that WIN 55,212 (used for convenience) acts the same as anandamide, see: Felder, et al; ibid.]

The data from this experiment is shown in Table 3 for the compound of Example 6. The agonist WIN 55,212 inhibits the N-type calcium channel via the CB-1 receptor, thus decreasing the current to the voltage clamp of −65 pA. The addition of a compound of formula I (Example 6) increases this current to −150 pA by opening the N-type calcium channel via the CB-1 receptor. Oxo-M and $Cd^{2+}$ are controls showing the specificity of the current regulation and the integrety of the cellular organelles.

Thus, this experiment demonstrates the ability of the compounds of formula I to regulate major nerve cell organelles by antagonizing the actions of either the endogenous ligand, anandamide or agonists in vitro.

TABLE 3

| Sample | Cell Current pA |
| --- | --- |
| Baseline | −150 |
| WIN 55,212 (WIN) (100 nM) | −60 |
| Cmpd. 6 (1 µM) | −150 |
| WIN + Cmpd. 6 | −150 |
| Oxo-M + Cmpd. 6 | −60 |
| $Cd^{++}$ | −60 |

In Vivo Effects of Anandamide Antagonists

The following experiment demonstrates the ability of the compounds of formula I to inhibit the sedation caused by anandamide in vivo and in a standard model (Open Field Assay) of mouse behavior, which has been a classic model for the evaluation of active and useful central nervous system agents.

The Open Field Assay evaluates the motion (both horizonal and vertical) of a mouse when placed in a large, open area. Specifically, C57BL/6J mice are injected with 20 mg/kg (i.p.) of the compound of Example 6, 28 minutes before injecting anandamide at 2 mg/kg (i.p.). The mouse is placed in the center of a large area of a device which measues the number of vertical and horizontal movements of the mouse (Digiscan Automated Open Field). Each test session is of 5 minute duration. At the end of this time period, the mouse is removed from the scanner and the recorded data are automatically analyzed and satisically evaluated. Further details are given in Crawley, J., J. Neurosci., 12(9), p. 3380–3391 (1992).

The results of this experiment are shown in Tables 4–5. As seen in the Tables, anandamide causes a severe depression and sedation of the animal's movements, which is reversed by the adminstration of the compound of Example 6 in regard to Horizontal Exploratory Activity and Total Distance Exploratory Behavior.

TABLE 4

Total Distance Exploratory Behavior

| Sample | Digiscan Total Distance/5 min. |
|---|---|
| Vehicle | 250* |
| Vehicle + Anandamide | 50 |
| Cmpd. 6 + Anandamide | 300* |

*p < 0.01

TABLE 5

Horizontal Exploratory Behavior

| Sample | Digiscan Horizontal Activity/5 min. |
|---|---|
| Vehicle | 1100* |
| Vehicle + Anandamide | 200 |
| Cmpd. 6 + Anandamide | 900* |

*p < .05

Applications

The compounds of formula I have been shown to bind to the human CB-1 receptor and to inhibit the cellular, signal-transduction events evoked by both anandamide and cannabinoids. In vivo, the compounds have been shown to mitigate the effects of anandamide in the mouse. Due to the localization of the CB-1 receptor in the hipocampus and the known pharmacology of the cannabinoids and their correspondence with anandamide (see: Howlett, A. C., et al., TINS, 13(10),p. 420–423.(1990)), mammals, including humans, suffering from symptomology similar to that seen with cannibinoids, would recieve benefit from an antagonist of the CB-1 receptor (a compound of formula I). Many disease states, although caused by different etiologies, have common symptomology. The disease states (listed in the applications, below) are not caused by the use or abuse of cannibinoids, but since their symptoms are so similar, the endogenous factor anandamide would seem to be a likely contributory factor. Thus, a compound of formula I would be of benefit in the treatment of the symptomology of many diseases. Additionally, since treatment of symptomology and treatment of the causal factors of a disease and their interaction are not well understood or, indeed, may not be separate pathologies, it should not be construed that this invention would be solely limited to the treatment of symptoms.

Symptoms, which would be benecially effected in mammals, including humans, with a compound of formula I, would include, but not be limited to: depression, loss of cognitive function, loss of mental alertness, loss of memory, and loss of sensory perception. These symptoms occur in a variety of pathological states, syndromes, and diseases. The extent, magnitude, particulars of these symptoms vary widely both between disease states and between various individuals suffering from one of those diseases.

Listed, below, are some of the diseases, from which mammal, including a human, would derive a benefit from a compound of formula I: Alzheimer's Disease, head trauma, senile dementia, brain tumors, and the like. Additional, disease states which may be included in this catagory are elaborated in volumenous references in the art, e.g., see: "Harrison's Priciples of Internal Medicine", Isselbacher, K. J., et all. Eds. 9th Ed., McGraw-Hill Book Co., New York, 1980, Section 3, "Alterations in Nervous Function". Again, due to variability of symptoms in any of these diseases, the decision of the use, dosage level, and protocol of treatment of a compound of this of this invention is at the discretion of the attending physician.

We claim:

1. A compound of the formula:

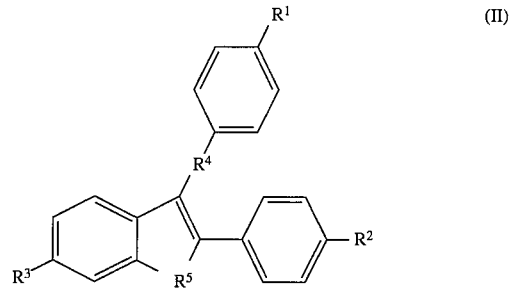

Wherein $R^1$ is cyano;

$R^2$ and $R^3$ are each individually, $C_1$–$C_4$ alkyl or $C_1$–$C_4$ alkoxy;

$R^4$ is carbonyl; and $R^5$ is oxygen or sulfur.

2. The compound of claim 1 wherein $R^2$ and $R^3$ are both methoxy and $R^5$ is —O—.

3. The compound of claim 1 wherein $R^2$ is methyl, $R^3$ is methoxy and $R^5$ —O—.

4. The compound of claim 1 wherein $R^2$ and $R^3$ are both methoxy and $R^5$ is —S—.

5. A pharmaceutical formulation comprising an effective amount of a compound of claim 1, and a pharmaceutically acceptable carrier, excipient or diluent thereof.

* * * * *